United States Patent [19]

Boehm et al.

[11] Patent Number: 4,769,473

[45] Date of Patent: Sep. 6, 1988

[54] 1-HYDROXYPYRAZOLE-4-CARBOXYLIC ACID

[75] Inventors: Heinrich Boehm, Neuhofen; Norbert Rieber, Mannheim, both of Fed. Rep. of Germany

[73] Assignee: BASF Aktiengesellschaft, Ludwigshafen, Fed. Rep. of Germany

[21] Appl. No.: 901,583

[22] Filed: Aug. 29, 1986

[30] Foreign Application Priority Data

Sep. 14, 1985 [DE] Fed. Rep. of Germany ....... 3532879

[51] Int. Cl.$^4$ .......................................... C07D 231/14
[52] U.S. Cl. .................................................... 548/377
[58] Field of Search ......................................... 548/377

[56] References Cited

U.S. PATENT DOCUMENTS 4,350,819  9/1982  Rieber et al. ...................... 548/375

FOREIGN PATENT DOCUMENTS 816531  7/1959  United Kingdom ................ 548/378

Primary Examiner—Mary Lee
Assistant Examiner—Kurt G. Briscoe
Attorney, Agent, or Firm—Keil & Weinkauf

[57] ABSTRACT

1-Hydroxypyrazole-4-carboxylic acid is prepared by heating an alkali metal of alkaline earth metal salt of 1-hydroxypyrazole, or a mixture of 1-hydroxypyrazole with an alkali metal or alkaline earth metal carbonate or bicarbonate, at from 120° to 250° C. for from 1 to 40 hours under a $CO_2$ pressure of 20–300 bar, and is used for the preparation of pharmacologically useful compounds.

1 Claim, No Drawings

1-HYDROXYPYRAZOLE-4-CARBOXYLIC ACID

The present invention relates to 1-hydroxypyrazole-4-carboxyic acid, its preparation and its use for the preparation of pharmacologically useful compounds.

The literature (H. Kolbe, Liebigs Ann. Chem. 113 (1860), 125) discloses the reaction of phenols with $CO_2$ in the presence of an alkali metal carbonate to give phenolcarboxylic acids. Potassium pyrrolide undergoes a similar reaction with $CO_2$ to give the potassium salt of 2-pyrrolecarboxylic acid.

German Laid-Open Application DOS No. 3,031,385 describes the preparation of 1-hydroxypyrazole.

We have found, surprisingly, that 1-hydroxypyrazole-4-carboxylic acid is advantageously obtained if an alkali metal or alkaline earth metal salt of 1-hydroxypyrazole, or a mixture of 1-hydroxypyrazole with an alkali metal or alkaline earth metal carbonate or bicarbonate, is heated at from 120° to 250° C. for from 1 to 40 hours under a $CO_2$ pressure of 20–300 bar.

The reaction may be represented by, for example, the following equation:

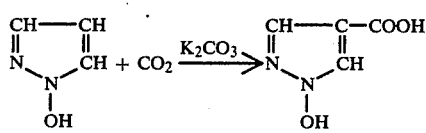

The reaction evidently does not take place similarly to that of the pyrrolide and could not be deduced from the latter reaction since there the carboxyl group is introduced in the α-position with respect to the nitrogen, while here it is introduced in the β-position.

The process according to the invention gives the novel 1-hydroxypyrazole compound by a simple route. This compound is used as a starting compound for pharmacologically useful substances (cf. parallel German Application P No. 35 32 880.0).

This application corresponds to U.S. Application Ser. No. 901,579, filed Aug. 29, 1986. The application discloses the use of the methyl ester of 1-hydroxypyrazol-4-carboxylic acid to produce novel compounds of the formula I

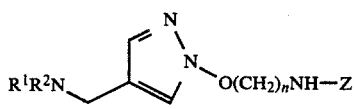

where $R^1$ and $R^2$ independently of one another are each hydrogen, lower alkyl or benzyl, or $R^1$ and $R^2$, together with the nitrogen atom to which they are bonded, may be a pyrrolidino, piperidino or morpholino radical, n is an integer from 2 to 5, and Z is a radical of the formula

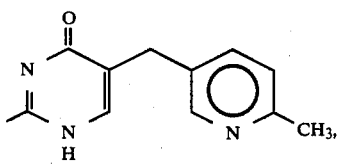

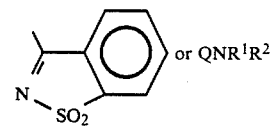

where $R^1$ and $R^2$ have the same meanings as above, Q is

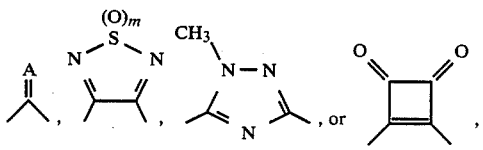

A is $CHR^3$ or $NR^3$ in which $R^3$ is CN, $NO_2$, $SO_2$-aryl or $SO_2$-lower alkyl, and m may be 0 or 1, and their pharmaceutically tolerated salts.

In a preferred group of compounds, n is 4.

In another preferred group of compounds, Z is

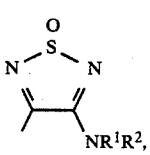

where $R^1$ is hydrogen and $R^2$ is hydrogen or lower alkyl. These compounds are useful as selective antagonists to histamine $H_2$ receptors. The novel compounds can be prepared, for example, by reacting the methyl ester of 1-hydroxypyrazole-4-carboxylic acid with a ω-substituted aldehyde-acetal of the formula

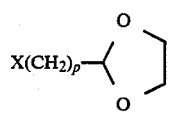
XXII where X is a leaving group such as a halogen and p is n-1 to form a compound of the formula

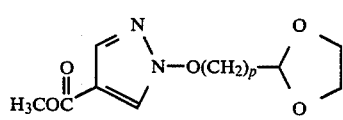
XXIII

The ester group of compound XXIII is then hydrolyzed to form the carboxylic acid and then converted to the amide with an amine of the formula VII $HNR^1R^2$          VII To do this, carboxylic acid is converted temporarily to an activated derivative, for example an acyl halide, an anhydride or an activated ester.

The intermediate of the formula XXIV

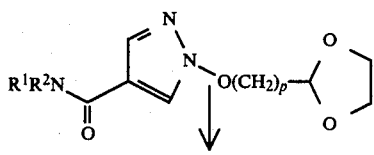

is converted with a dilute aqueous mineral acid in a conventional manner to the aldehyde XXV,

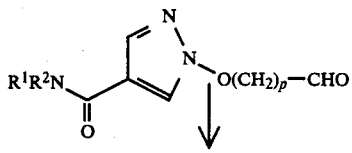

and the latter is reacted with hydroxylamine to give the oxime XXVI

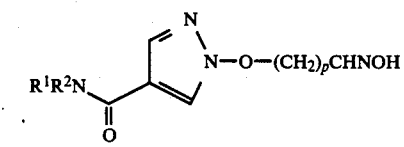

The oxime XXVI can be converted to the amine III

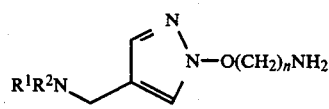

with suitable reducing agents, for example, complex metal hydrides, such as lithium aluminum hydride.

The amine III is reacted with a thio compound of the formula II

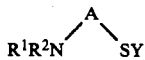

to form the compound of the formula I. The compounds of formula I are useful as selective antagonists to histamine $H_2$ receptors.

Suitable alkali metal and alkaline earth metal 1-hydroxypyrazolides and carbonates and bicarbonates are those of lithium, sodium, potassium, magnesium and calcium, the sodium and potassium compounds being preferred.

The reaction may be carried out as follows:

A mixture of 1-hydroxypyrazole and not less than an equivalent amount of sodium or potassium carbonate or the sodium or potassium salt of 1-hydroxypyrazole is reacted with $CO_2$ in the presence or absence of an inert solvent at from 120° to 250° C. for from 1 to 40 hours under a $CO_2$ pressure of 20–300 bar. After the pressure has been let down, the end product is isolated in a conventional manner by acidification followed by filtration or extraction, and, if necessary, is purified by recrystallization. Suitable solvents are polar protic and aprotic solvents, eg. water, alcohols, dimethylformamide, acetonitrile or tertiary amines.

In the Examples which follow, parts are by weight.

EXAMPLE 1 part of 1-hydroxypyrazole is mixed thoroughly with 4 parts of potassium carbonate, and the mixture is introduced into an autoclave. Carbon dioxide is forced in at room temperature until the pressure reaches 50 bar, after which heating is carried out for 20 hours at 150° C. The reactor content is then dissolved in water, the solution is acidified with hydrochloric acid, which precipitates the 1-hydroxypyrazole-4-carboxylic acid, and the latter is filtered off and recrystallized from water. 0.68 part (45% of theory) of 1-hydroxypyrazole-4-carboxylic acid of melting point 230° C. is obtained.

We claim:

1. 1-Hydroxypyrazol-4-carboxylic acid (I)

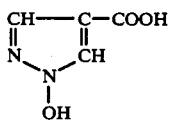

* * * * *